United States Patent
Mayahara et al.

(10) Patent No.: US 11,028,047 B2
(45) Date of Patent: Jun. 8, 2021

(54) METHOD FOR RECOVERING DIMETHYL SULFOXIDE FROM RECOVERED RESIST REMOVER

(71) Applicant: KURARAY CO., LTD., Kurashiki (JP)

(72) Inventors: Kunio Mayahara, Chiyoda-ku (JP); Koji Tamura, Kamisu (JP); Akinobu Takeda, Kamisu (JP)

(73) Assignee: KURARAY CO., LTD., Kurashiki (JP)

( * ) Notice: Subject to any disclaimer, the term of this patent is extended or adjusted under 35 U.S.C. 154(b) by 0 days.

(21) Appl. No.: 16/630,630

(22) PCT Filed: Jul. 31, 2018

(86) PCT No.: PCT/JP2018/028539
§ 371 (c)(1),
(2) Date: Jan. 13, 2020

(87) PCT Pub. No.: WO2019/026868
PCT Pub. Date: Feb. 7, 2019

(65) Prior Publication Data
US 2020/0131122 A1 Apr. 30, 2020

(30) Foreign Application Priority Data
Aug. 2, 2017 (JP) .................. JP2017-149846

(51) Int. Cl.
*B01D 3/34* (2006.01)
*C07C 315/06* (2006.01)
*C07C 29/80* (2006.01)

(52) U.S. Cl.
CPC .............. *C07C 315/06* (2013.01); *B01D 3/34* (2013.01)

(58) Field of Classification Search
CPC ......... C07C 29/80; C07C 29/92; C07C 29/84; C07C 315/06; G03F 7/42; G03F 7/422; G03F 7/423; G03F 7/425; G03F 7/426
See application file for complete search history.

(56) References Cited

U.S. PATENT DOCUMENTS

| | | | |
|---|---|---|---|
| 5,925,224 A * | 7/1999 | Kobayashi | B01D 5/006 203/47 |
| 8,263,539 B2 * | 9/2012 | Phenis | C11D 7/32 510/176 |
| 8,961,744 B2 * | 2/2015 | Lee | B01D 5/006 203/47 |
| 9,069,259 B2 * | 6/2015 | Phenis | G03F 7/426 |
| 9,168,468 B2 * | 10/2015 | Lee | B01D 5/0072 |
| 2007/0111912 A1 * | 5/2007 | Phenis | C11D 1/004 510/175 |
| 2009/0047609 A1 | 2/2009 | Atkinson et al. | |
| 2009/0186793 A1 * | 7/2009 | Phenis | C11D 3/26 510/176 |
| 2013/0172225 A1 * | 7/2013 | Phenis | G03F 7/425 510/176 |
| 2014/0083458 A1 * | 3/2014 | Fuchigami | G03F 7/425 134/12 |
| 2014/0238840 A1 * | 8/2014 | Lee | B01D 5/006 203/32 |
| 2015/0129409 A1 * | 5/2015 | Lee | B01D 3/106 202/161 |

FOREIGN PATENT DOCUMENTS

| | | |
|---|---|---|
| CN | 102219272 A | 10/2011 |
| JP | 9-278743 A | 10/1997 |
| JP | 2004-43434 A | 2/2004 |
| JP | 2005-288329 A | 10/2005 |
| JP | 2006-69960 A | 3/2006 |
| JP | 2010-537231 A | 12/2010 |
| KR | 10-2009-0025102 A | 3/2009 |
| WO | WO 2010/073430 A1 | 7/2010 |

OTHER PUBLICATIONS

International Search Report dated Sep. 11, 2018 in PCT/JP2018/028539 filed on Jul. 31, 2018, 2 pages.
Singapore Official Action dated Feb. 17, 2021, in Singapore Patent Application No. 11202000860W.

* cited by examiner

*Primary Examiner* — Jonathan Luke Pilcher
(74) *Attorney, Agent, or Firm* — Oblon, McClelland, Maier & Neustadt, L.L.P.

(57) ABSTRACT

A method for recovering dimethyl sulfoxide, including a step of contacting a recovered resist remover containing at least one compound selected from the group consisting of glycol ether, glycol and triol, and dimethyl sulfoxide with water and performing distillation.

9 Claims, No Drawings

METHOD FOR RECOVERING DIMETHYL SULFOXIDE FROM RECOVERED RESIST REMOVER

TECHNICAL FIELD

The present invention relates to a method for recovering dimethyl sulfoxide (DMSO) from a recovered resist remover.

BACKGROUND ART

When a semiconductor element or the like is manufactured by photolithography, after a fine circuit or the like is formed by etching, an unnecessary resist film or an etching residue is washed and removed by using a resist remover. As the resist remover, an aqueous solution of sodium hydroxide or a general organic solvent can be used alone, but the peelability is not sufficient, and a variety of resist removers have been proposed so far in order to improve the peelability.

As a resist remover having high peelability, for example, a solution obtained by dissolving a quaternary ammonium hydroxide such as tetramethylammonium hydroxide (TMAH) in a mixed solvent of DMSO and glycol ether such as 3-methoxy-3-methyl-1-butanol (MMB) is often used (PTL 1).

CITATION LIST

Patent Literature

PTL 1: WO 2010/073430 A1

SUMMARY OF INVENTION

Technical Problem

Currently, used resist removers (recovered resist removers) are usually discarded as industrial waste. On the other hand, DMSO used in the resist remover as described above is also used as a rinse liquid in a rinse process after resist peeling, and the amount of the DMSO to be used has increased remarkably in recent years. Therefore, if high purity DMSO can be recovered from a recovered resist remover and reused, it is advantageous in terms of cost and the like.

However, DMSO (boiling point 189° C.) and glycol ether and the like are often close in boiling point (for example, MMB has a boiling point of 174° C.), and it is difficult to recover high purity DMSO by a method such as ordinary vacuum distillation, and the reuse of DMSO was not realistic.

An object of the present invention is to provide a method for efficiently recovering high purity DMSO from a recovered resist remover at a low cost.

Solution to Problem

As a result of intensive studies, the present inventors have found that high purity DMSO can be efficiently recovered at a low cost by adding water to a recovered resist remover and performing distillation, and the present invention has been completed through further studies based on the findings.

The present invention relates to the following [1] to [3].

[1] A method for recovering DMSO, including a step of contacting a recovered resist remover containing at least one compound selected from the group consisting of glycol ether, glycol and triol, and DMSO with water and performing distillation.

[2] The recovering method according to [1], wherein the compound is at least one selected from the group consisting of 3-methoxy-3-methyl-1-butanol, diethylene glycol, propylene glycol, glycerin and 2-(2-methoxyethoxy)ethanol.

[3] The recovering method according to [1], wherein the compound is 3-methoxy-3-methyl-1-butanol.

Advantageous Effects of Invention

According to the method of the present invention, high purity DMSO can be efficiently recovered from a recovered resist remover at a low cost.

DESCRIPTION OF EMBODIMENTS

The method of the present invention will be described in detail below.

In the present invention, the "recovered resist remover" as a target for recovering DMSO typically refers to a used resist remover after washing and removing an unnecessary resist film or the like in photolithography, and includes at least one compound selected from the group consisting of glycol ether, glycol and triol, and DMSO.

Usually, the recovered resist remover also includes a quaternary ammonium hydroxide, a resist component, and the like.

Examples of the glycol ether include ethylene glycol monomethyl ether, ethylene glycol monoethyl ether, ethylene glycol monobutyl ether, diethylene glycol monomethyl ether, diethylene glycol monoethyl ether, diethylene glycol monopropyl ether, diethylene glycol monobutyl ether, triethylene glycol monomethyl ether, 3-methoxy-3-methyl-1-butanol (MMB), dipropylene glycol monomethyl ether, and 2-(2-methoxyethoxy)ethanol.

Examples of the glycol include ethylene glycol, propylene glycol, diethylene glycol, dipropylene glycol, and triethylene glycol.

Examples of the triol include glycerin.

Among these, the compound is preferably at least one selected from the group consisting of MMB, diethylene glycol, propylene glycol, glycerin and 2-(2-methoxyethoxy)ethanol, and more preferably MMB.

Examples of the quaternary ammonium hydroxide include tetramethylammonium hydroxide (TMAH), tetraethyl ammonium hydroxide, tetrapropylammonium hydroxide, tetrabutylammonium hydroxide, trimethylethylammonium hydroxide, dimethyldiethylammonium hydroxide, trimethyl (2-hydroxyethyl) ammonium hydroxide, triethyl (2-hydroxyethyl) ammonium hydroxide, and spiro-[1,1']-bipyrrolidinium hydroxide.

Among these, the quaternary ammonium hydroxide is preferably at least one selected from the group consisting of TMAH, tetrapropylammonium hydroxide, and spiro-[1,1']-bipyrrolidinium hydroxide, and more preferably TMAH.

The recovered resist remover may contain water, alkanolamines, an amino acid, a surfactant, an antifoaming agent, or the like as the other components.

In the method for recovering DMSO of the present invention, the recovered resist remover is brought into contact with water and then distillation is performed. Thus, at least one compound selected from the group consisting of glycol ether, glycol and triol can be first distilled out, and then high purity DMSO can be distilled out.

The contact between the recovered resist remover and water can be carried out by, for example, mixing the recovered resist remover and water. As a specific method when the recovered resist remover is brought into contact with water to perform distillation, for example, a method of adding water to the recovered resist remover and performing distillation can be exemplified. In carrying out such a method of adding water to the recovered resist remover and performing distillation, water may be added to the recovered resist remover at once, followed by distillation, or distillation may be performed while adding water intermittently or at a constant rate.

The temperature at the time of distillation is preferably in the range of 30 to 250° C., and more preferably in the range of 50 to 230° C. The distillation may be carried out under normal pressure or under reduced pressure.

The amount of water added is preferably in the range of 0.1 to 100 parts by mass, and more preferably in the range of 0.1 to 10 parts by mass, with respect to 1 part by mass of the recovered resist remover.

EXAMPLES

Hereinafter, the present invention will be described in detail by examples and the like, but the present invention is not limited by these examples.

Example

To a 500 mL three-necked flask equipped with a Helipack 50 cm distillation column (distillation stage number: 7 stages), a mixture of 70 g DMSO and 30 g MMB was added as a recovered resist remover. 300 g of water was added thereto, and distillation was carried out under conditions of an internal temperature of 104 to 140° C., and normal pressure. When the distillate disappeared, DMSO was distilled out under conditions of an internal temperature of 120 to 130° C. and 2 to 10 mmHg to obtain 62.2 g of DMSO having a purity of 99.9% (yield 88.9%).

Comparative Example

A similar operation was carried out as in Example, except that water was not added. As a result, 22.3 g of DMSO having a purity of 82.3% was obtained.

Although the above Example and Comparative Example are the tests on the conditions which do not contain quaternary ammonium hydroxide and resist components that are considered to be normally contained in the actual recovered resist remover, these components are considered not to be distilled by distillation, so that the above Example and Comparative Example function sufficiently as model tests.

From the results of Example and Comparative Example, it can be seen that in accordance with the method of the present invention, high purity DMSO can be efficiently recovered from a recovered resist remover at a low cost.

INDUSTRIAL APPLICABILITY

According to the method of the present invention, high purity DMSO can be efficiently recovered from a recovered resist remover at a low cost, which is useful in that DMSO which has been conventionally discarded can be reused.

The invention claimed is:

1. A method for recovering dimethyl sulfoxide from a composition, the method comprising:
    contacting the composition with water, where the composition comprises at least one compound selected from a group consisting of glycol ethers, glycols, and triols, and dimethyl sulfoxide;
    and performing distillation on the composition contacted with water to recover a purified dimethyl sulfoxide product,
    wherein an amount of the water contacted with the composition is from 0.1 to 100 parts by mass with respect to 1 part by mass of the composition.

2. The method according to claim 1, wherein the at least one compound is selected from a group consisting of 3-methoxy-3-methyl-1-butanol, diethylene glycol, propylene glycol, glycerin and 2-(2-methoxyethoxy)ethanol.

3. The method according to claim 1, wherein the at least one compound is 3-methoxy-3-methyl-1-butanol.

4. The method according to claim 1, wherein the composition is a resist remover that has been used to wash and remove an unnecessary resist film in photolithography.

5. The method according to claim 1, wherein the composition further comprises a quaternary ammonium hydroxide, a resist component, or both.

6. The method according to claim 5, wherein the composition further comprises at least one other component selected from a group consisting of water, alkanolamines, amino acids, surfactants, and antifoaming agents.

7. The method according to claim 1, wherein the distillation is performed such that the purified dimethyl sulfoxide product has a purity of 99.9%.

8. The method according to claim 1, wherein a purity of the purified dimethyl sulfoxide product obtained by the distillation is higher than a purity of a dimethyl sulfoxide product obtained by distilling the composition without contacting with water.

9. The method according to claim 1, wherein the distillation is performed at a temperature of from 104 to 250° C.

* * * * *